United States Patent [19]
Yamato et al.

[11] Patent Number: 5,232,769
[45] Date of Patent: Aug. 3, 1993

[54] MICROCAPSULE, TREATING LIQUIDS CONTAINING THE SAME, AND TEXTILE STRUCTURE HAVING MICROCAPSULES ADHERING THERETO

[75] Inventors: Yoshihisa Yamato, Shiki; Takashi Yoshida, Yokohama; Masaru Kikuchi, Tokyo; Mihoko Okamoto, Fujisawa; Kyoji Miyoshi; Shigeru Fukuda, both of Hofu; Toshikazu Fuse, Nagahama; Toshio Yamauchi, Osaka; Yasuhiro Ogawa, Suita; Shogo Mutagami; Shigeo Shiomura, both of Hofu; Yoshikatsu Mizukami, Osaka, all of Japan

[73] Assignee: Kanebo, Ltd., Tokyo, Japan

[21] Appl. No.: 667,405

[22] PCT Filed: Jul. 31, 1990

[86] PCT No.: PCT/JP90/00981
§ 371 Date: Mar. 29, 1991
§ 102(e) Date: Mar. 29, 1991

[87] PCT Pub. No.: WO91/01801
PCT Pub. Date: Feb. 21, 1991

[30] Foreign Application Priority Data

| Aug. 1, 1989 | [JP] | Japan | 1-201054 |
| Aug. 1, 1989 | [JP] | Japan | 1-201056 |
| Aug. 1, 1989 | [JP] | Japan | 1-201058 |
| Aug. 2, 1989 | [JP] | Japan | 1-200967 |
| Aug. 3, 1989 | [JP] | Japan | 1-202098 |
| Oct. 3, 1989 | [JP] | Japan | 1-259579 |
| Oct. 11, 1989 | [JP] | Japan | 1-264195 |
| Jun. 7, 1990 | [JP] | Japan | 2-149666 |

[51] Int. Cl.[5] ............ B32B 5/16; B32B 33/00
[52] U.S. Cl. .................. 428/240; 2/239; 5/482; 57/241; 57/250; 57/258; 424/402; 428/247; 428/248; 428/252; 428/253; 428/283; 428/288; 428/290; 428/320.2; 428/321.5; 428/341; 428/361; 428/378
[58] Field of Search ............... 428/240, 245, 281, 283, 428/288, 289, 290, 341, 320.2, 321.5

[56] References Cited

FOREIGN PATENT DOCUMENTS

| 0963808 | 3/1975 | Canada. |
| 2055019 | 11/1970 | Fed. Rep. of Germany. |
| 54-16566 | 6/1979 | Japan. |
| 54-73510 | 4/1984 | Japan. |
| 61-224962 | 6/1986 | Japan. |
| 62-12707 | 1/1987 | Japan. |
| 1275969 | 6/1972 | United Kingdom. |
| 1401143 | 7/1975 | United Kingdom. |

Primary Examiner—James C. Cannon
Attorney, Agent, or Firm—Flynn, Thiel, Boutell & Tanis

[57] ABSTRACT

This invention relates to a microcapsule having a particle diameter of 2~300 μm and comprising a substance acting to improve physiological conditions of human skin, for example, substances exhibiting such effects as skin whitening, aging preventive, humidity preservable, itch suppressive, pain-killing, or antiphlogistic ones, and/or aromatic agents contained within the filmy coating of synthetic high molecular substance. The microcapsule is not broken when making, processing, or laundering the textile structure, but is gradually broken when the textile structure is put on the human body, used for another purpose, or subjected to intentional application of friction or pressure thereto, and sustainedly releases acting substances contained therein. Treatment liquids comprising these microcapsules and binder, preferably containing a spraying agent, adapt the microcapsules to tightly adhere to textile structures such as stockings underwear, and bedclothes, thereby providing a textile structure to exhibit the aforesaid effects.

11 Claims, No Drawings

MICROCAPSULE, TREATING LIQUIDS CONTAINING THE SAME, AND TEXTILE STRUCTURE HAVING MICROCAPSULES ADHERING THERETO

DESCRIPTION

1. Technical Field

The present invention relates to microcapsules encapsulating a substance having a function to improve physiological conditions of human skin, such as vitamin C, vitamin E, seaweed extracts, antipruritics and analgesics, and/or aromatic agents; treating liquids containing such microcapsules; and textile structures treated with such a treating liquid, particularly apparel which are worn contacting directly with human skin, such as stockings, socks, underwear or the like, bedclothes or medical auxiliary materials.

2. Background Art

Hitherto in the cosmetic field, etc., there have come into the market articles with the object of skin whitening, such as whitening creams, whitening packs or the like, namely, cosmetics incorporated with vitamin C (ascorbic acid) efficacious against melanopathy and can maintain a fair and fresh complexion by protecting the skin against speckling, freckling or the like. There also have been placed on the market articles with an object of moisturizing the skin, such as humidity preservable creams, humidity preservable packs or the like, namely, cosmetics incorporated with algae colloid, i.e., a seaweed extract, as an active principle having a moisturizing effect to prevent drying of the skin, which could realize a soft, young and fresh skin by moisturizing the skin.

Thus, recently, importance is being attached to the skin-care of hands and feet equal to the skin-care of faces, so that whitening lotions or the like incorporated with vitamin C or seaweed extracts have appeared for application to arms or legs.

However, lotions or creams, such as the abovementioned type to be left as they have once been applied to the surface of the skin, are directed to use after bathing, before sleeping or the like, and have not given a certain sustained function to the skin. Accordingly, it is the present situation that, in general, skin-care from going out in the morning until coming home has not been taken into consideration.

Pharmaceuticals with an object of analgesic, antiphlogistic or antipruritic effects have so far been developed in diversified dosage forms such as internal medicine, injection, ointment or plaster, and many have been placed on the market. For example, in Japanese Patent Application Laid-open No. 60-188,314, there are described antipruritic plasters comprising an ointment compounded with crotaminton as an antipruritic active principle, and in Japanese Patent Application Laid-open No. 60-178,837, there are described oral-administrable gelatine capsules encapsulating an anti-SRS-A agent However, these administration methods have not always been effective, as one feels uncomfortableness inherent in ointments when one has no pain or itch, one cannot be given selectivity in acting position or fast-acting effects when one feels pain or itch, feels uncomfortableness and harm inherent in injection, or the like. Further, as technology to utilize microcapsules, there have been proposed a method of applying a mixture of microcapsules encapsulating a liquid toilet preparation with a size containing a melamine resin to textile articles (British Patent Specification No. 1,401,143); a method for preparing fragrant towel fabrics by applying a liquid mixture of aromatic-containing microcapsules with an acrylic resin to towel fabrics (Japanese Patent Application Laid-open No. 58-4,886); a process for preparing fragrance-emitting printed articles, by printing a printing paste comprising microcapsules composed of a filmy starch envelope encapsulating an aromatic agent, a thermoplastic material and a thickening agent (Japanese Patent Applications Laid-open Nos. 53-47,440 and 53-49,200); and the like However, there have not yet been disclosed microcapsules encapsulating the above-mentioned material functionable to improve physiological conditions of the skin, such as vitamins, seaweed extracts, analgesics, antipruritics or the like (hereinafter, may be referred to as "skin-improver").

Further, as a hitherto proposed pillow having a fragrance, there have been those having a pillow-case coated with a resin containing an aromatic agent or those with a sachet or scent paper attached thereto In Japanese Patent Application Laid-open No. 61-63,716, there has been also proposed a fragrant core and sheath type composite filament comprising a core incorporated with a dispersion of an aromatic agent and having a cavity in the core. However, there has been a problem such that the aromatic agent is prone to volatilize or deteriorate at a high temperature, so that aromatic agents endurable to melt-spinning are limited. Alternatively, application by transfer-printing method, as disclosed in Japanese Patent Application Laid-open No. 53-106,885, also cannot provide sufficiently a long-lasting fragrance. Further, problems also have arisen such that the binder permeates into woven or knitted yarns, resulting in a very stiff feel, or the transfer-printed portions have a different feel and are detached by washing, etc. Namely, the above-mentioned fragrant pillows have had a serious drawback such as poor resistance to washing. In order to enhance the resistance to washing, it is required to increase the amount of resin coating, wherefore the feel of the pillow cases has been considerably impaired.

Disclosure of Invention

A principal object of the present invention is to improve very naturally and continuously, physiological conditions of the skin.

Another object is to provide apparel, particularly such as stockings, underwear or the like, which contacts directly with the skin and gradually releases a skin-improver by movement or action of the human body while it is worn, to give a long-lasting, whitening, humidity preserving, pain-killing, antipruritic or the like effect to the skin.

Further another object is to provide textile fabrics, or made-up articles or laminated sheet materials thereof which can attain "pain-killing or antipruritic effect when required".

A further different object is to provide a treating liquid containing a skin-improver or an aromatic agent which is excellent in resistance to washing and, further, a spray of the treating liquid containing a propellant.

The above-described objects can be achieved by a microcapsule characterized by encapsulating at least a substance having a function of improving physiological conditions of human skin, having a particle diameter within the range of 2-300 μm and being composed of a wall membrane comprising a synthetic high molecular material The above-mentioned substance is preferably at least one skin-improver selected from the group consisting of ascorbic acids, tocopherols, seaweed extracts, analgesics and antipruritics.

The above-mentioned synthetic high molecular material comprises preferably a formaldehyde resin as a main component.

The present invention includes a treating liquid characterized by containing microcapsules encapsulating a substance having a function of improving physiological conditions of human skin and having a particle diameter within the range of 2-300 μm and a wall membrane comprising a synthetic high molecular material, and a binder, at a weight ratio of 10:1~1:5.

Such a treating liquid can be a spray containing a propellant.

The above-mentioned binder contained in the treating liquid of the present invention is preferably a silicone based resin or urethane based resin.

The present invention further includes textile structures characterized by having microcapsules encapsulating a substance having a function of improving physiological conditions of human skin and having a particle diameter within the range of 2-300 μm and a wall membrane comprising a synthetic high molecular material, adhering thereto with a binder, a weight ratio of said microcapsules to said binder being in the range of 10:1~1:5 and the total amount of said microcapsules and said binder adhering to the structure being 0.3~15% based on the weight of fibers in the adhering portion.

Typical textile structures of the above include stockings.

Additionally, underwear is also important as the textile structure of the present invention.

As another embodiment of the present invention, mention may be made of a textile sheet characterized in that a first textile fabric having the microcapsules adhering thereto is laminated on a second textile fabric or sheet.

A further different embodiment of the present invention is a microcapsule characterized by encapsulating an aromatic agent and having a particle diameter within the range of 5-30 μm and a wall membrane comprising a formaline based resin as a main component.

Such a microcapsule encapsulating an aromatic agent can be mixed with a resinous binder at a weight ratio of 10:1~1:5 to prepare a fragrance processing liquid.

This processing liquid is preferred to be applied in the form of a spray further containing a propellant.

As ascorbic acids to be employed in the present invention, mention may be made of any known compounds comprising ascorbyl palmitate, ascorbyl stearate, ascorbyl dipalmitate, ascorbic acid phosphate magnesium salt, or the like. Particularly, ascorbyl dipalmitate is preferred in respect of whitening effect and feasibility in microencapsulating, which has a good endermic absorbability and high safety for skin, acts effectively as an ascorbic acid source and has been generally utilized as a material for compounding medicated cosmetics for which physiological effects of ascorbic acids are expected.

As tocopherols to be applied to the present invention, mention may be made of α-tocopherol, β-tocopherol, γ-tocopherol and δ-tocopherol, which function to restrain aging of the skin that is otherwise accelerated by peroxide lipid as well as to activate skin and also to prevent melanosis.

The seaweed extracts to be employed in the present invention are to mean, for example, those obtained by extracting dry powder of the genus Laminaria belonging to the class Phaeophycease with JSCI purified water and adding JSCI 1,3-butylene glycol thereto. The laminaria contains abundant vitamins, proteins and saccharides, in addition to minerals, such as calcium, phosphorus, iodine or the like, and is generally known to function to enhance humidity preserving action and metabolism.

As antipruritics to be employed in the present invention, mention may be made of known compounds, such as clemizole sulfate, isothipendyl hydrochloride, diphenhydramine and its derivatives, hydrocortisone, prednisolone and its homologues, fluorometholone, fluocinolone acetonide, formocortal, fludroxycortide, fluocinonide, flumetasone pivalate, triamcinolone, dexamethasone, betamethasone valerate, beclometasone dipropionate, guaiazulene, crotamiton, camphor, zinc white, indometacin, flufenamic acid, ibuprofen or the like. These are used alone or in combination.

As analgesics to be employed in the present invention, mention may be made of known pharmaceuticals to be used for muscle ache, contusion ache, neuralgia and stiffness, such as salicylic acid derivatives, such as methyl salicylate or the like, tocopherol acetate, diphenhydramine and its derivatives, zinc oxide, λ-menthol, camphor, or the like. These are used alone or in combination.

As an aromatic agent to be employed in the present invention, mention may be made of benzoin, cypress oil, ilang-ilang oil, fennel oil, neroli oil, chamomile oil, cardamon oil, clary sage oil, black pepper oil, cedar wood oil, jasmine oil, juniper oil, camphor, geranium oil, olibanum oil, basil oil, patchouli oil, rose oil, hyssop oil, sandalwood oil, pennyroyal oil, peppermint oil, bergamot oil, marjoram, melissane, myrrh, eucalyptus oil, lavender oil, rosemary oil and the like. For pillows, the jasmine oil, rose oil and sandalwood oil are preferred.

The wall membrane of the microcapsule according to the present invention is composed of a synthetic high molecular material comprising, as a main component, a thermosetting resin such as a formaline based resin, a polyester resin or the like (at least 50% by weight), preferably a urea-formaline based resin, a melamine-formaline based resin, and excellent in resistances to heat, pressure and water. Other than the above, acrylic resins (usable in combination with a cross-linking agent such as methylene-bis-acrylamide, divinyl compounds or the like), vinyl chloride based resins and cellulosic resins also can be used. The particle diameter of the microcapsule is generally within the range of 2-300 μm, and when it adheres to fiber, it is preferred to be within the range of 4-40 μm, which is smaller than the diameter of single fiber. Particularly when an aromatic agent is contained or the microcapsules adhere to stockings, the range of 5-20 μm is preferred Further, these microcapsules are preferred to withstand pressure or friction during processing or washing, and to have such a strength that the microcapsules may be broken or cracked little by little after adhering to textile articles, when the textile articles are worn or by an intentional friction Alternatively, the percent of the wall membrane is generally 3-60 weight % based on the weight of the microcapsule and when the microcapsule is made to adhere to a fiber, it is preferred to be within the range of 5–50 weight %. Particularly when it is made to adhere to a stocking, the range of 5–25 weight % is preferred.

Furthermore, the percent of the aromatic agent contained is 10–90 weight % and the thickness of the membrane is 0.3–4 μm, preferably 0.5–2 μm.

The composition of the microcapsule containing a skin-improver to be employed in the present invention is not specifically limited insofar as the microcapsule breaks to release the skin-improver by the action of an appropriate friction as mentioned above. However, low-formaline microcapsules are preferred.

The above-described microcapsules can be manufactured by known processes, such as an in situ polymerization process, an interfacial polymerization process or the like (for example, as disclosed in A. Kondo, "Microcapsules" in the Industrial Techno Library 25, published by Nikkan Kogyo Shimbusha, 1970, and Japanese Patent Application Publication No. 7724/1962). In the case of a formaline based resin wall membrane, a core component material compounded with at least a skin-improver or aromatic agent and urea or melamine are emulsified in water (using, as an emulsifier, sodium sulfonated polystyrene, polysodium acrylate, acrylic acid copolymer, maleic acid copolymer, polyvinyl alcohol, polyethylene glycol or the like, preferably at least acrylic acid copolymer or maleic acid copolymer particularly when the core component material comprises λ-menthol or peppermint oil; conducting pH control if required; and at a water temperature of 40° C.), then a formaline aqueous solution is added and the temperature is elevated to 70° C. while agitating, to conduct polycondensation reaction. Then, the produced microcapsules are filtered and dried to obtain the microcapsules containing a skin-improver or aromatic agent according to the present invention. Additionally, the size is controlled mainly by agitation power and concentration of the emulsifier, the percentage of the wall membrane is controlled mainly by the concentration of urea or melamine in oil droplets and the porosity of the wall membrane is controlled mainly by concentration of formaline (in order to make it dense, highly concentrated formaline is used) Furthermore, in order to dissolve or dilute the skin-improver, alcohols such as decyl alcohol, lauryl alcohol, glycerine or the like, esters such as lauryl stearate, palmitic acid glyceride or the like, natural oils such as peppermint oil, tsubaki oil, soybean oil, sesame oil, rape oil, coconut oil, clove oil, turpentine oil, beef tallow, eucalyptus oil or the like, can be incorporated additionally as a core component material (in this case, those incompatible with the wall membrane of the microcapsules should be selected).

The textile structures referred to in the present invention include yarns, staples, woven or knitted fabrics, nonwoven fabrics and secondary articles thereof, which may be composed of natural fibers, regenerated cellulosic fibers, synthetic fibers or mixtures thereof by blend spinning, plying, mix spinning, hybrid knitting or weaving, or the like. In connection with adhesion of binders, fibers having a rough surface, such as cotton, microporous fibers having microvoids or the like, or fibers having a compatibility with the binders are advantageous. The textile fabrics may be known fabrics such as woven, knitted or nonwoven fabrics or the like. Alternatively, as a sheet material, in addition to known films such as polyethylene films, polypropylene films or the like, papers including synthetic papers can be used.

Furthermore, the fibers to be employed in the present invention are preferred to be subjected in advance to a water-repelling pretreatment to prevent permeation of binders into knitting or weaving yarns or interstices of fabrics to stiffen the feel, so that the binder and microcapsules may adhere mainly to the surface of the fabrics and the feel inherent in fibers may not be impaired. As a water repelling treatment, known processes can be adopted. However, in the case of application of the products which requires no waterrepellency, they may be only impregnated with a relatively small amount of the treating agent followed by drying. For example, there is mentioned a process wherein an emulsion prepared by admixing aluminum acetate and paraffin with an emulsifier and a protective colloid is incorporated and dried, a process wherein an emulsion prepared by admixing methyl hydrogen polysiloxane with an emulsifier and a metallic soap is incorporated, dried and heat-treated, or the like.

The textile structures treated with a skin-improver according to the present invention can be used as underwear, stockings, socks, pajamas, gauze, bandages, supporters, sheets or tapes laminated with textile fabrics or films, or the like.

The stocking that is a typical textile structure to which the present invention is applied to is to mean collectively all stockings, such as overknee stockings, full-length stockings up to groin, panty stockings comprising integrally united panty and stocking portions, and the like Its material may be selected from any of synthetic fibers such as nylon fibers, polyester fibers or the like, and natural fibers such as cotton fibers, or the like. The knitting texture is also not specifically limited.

Further, the clothing to wear directly contacting with skin, such as lingerie, foundation, leotards, T-shirts or the like, and bedclothes to contact with skin, such as mattress covers, sheets, pillows or the like, are also as important in the present invention as the above-described stockings.

As a preferable processing process of such textile structures, mention may be made of a process wherein a treating liquid containing microcapsules encapsulating a skin-improver admixed with a resinous binder is applied to a textile structure, for example, a textile fabric or apparel, subjected in advance to water-repelling pretreatment, by means of soaking, padding, coating, spraying or printing.

The binder is not specifically limited insofar as it is a known resin such as silicone based, urethane based, vinyl acetate based, acrylic based, vinyl chloride based, phenolic based or the like, or a known sizing agent such as processed starch or the like. However, silicone based, urethane based or the like resins forming a rubbery film are preferred in respects of durability and pressure absorbability. In particular, the silicone based resinous binders display a coating effect and play a role as an adhesive between microcapsules containing a skin-improver and knitted fabrics and, inter alia, a silicone based aqueous emulsion type which is excellent in water-dispersibility and can be diluted readily with water, for example, an emulsion comprising, as a main ingredient, an organopolysiloxane emulsified with an emulsifier, is preferred. This hardens upon removal of water, to form a rubbery film having characteristics of a silicone rubber and exhibits an endurable bonding effect. Among the others, preferred are those which can be further dried and treated at 130° C. or less. Additionally, the resinous binders may be either of a solution type or an emulsion type. From the viewpoint of handling feasibility and price, an aqueous emulsion type is preferred. For example, silicone based resins, urethane based resins and vinyl acetate, since they harden upon removal of water to form rubbery films, display an endurable bonding effect and are most preferred.

The binder is applied in an amount of 0.1-5 times, preferably 0.02-2 times (by weight) that of the microcapsules and displays a sufficient bonding effect. If it is less than 0.1 time, the binding function extremely decreases, while even if it is applied in an amount of more than 5 times, the add-on percent of the microcapsules does not substantially change, inversely causing a problem in the soft feel fibers or fabrics, so that it is not preferred. Further, the total amount of both of them adhering usually occupies 0.3–15%, preferably 0.5–5.0% based on the weight of the fibers at the portion they adhere to. Namely, since the microcapsules adhere sufficiently to the fibers by applying a binder such as a silicone based resin or the like at the above-mentioned ratio, if the total amount of both of them adhering is less than 0.3% as specified above, both the skin-improving effect and durability are insufficient, while if it exceeds 15%, it affects the feel of the fibers and further the skin-improver releasing at one time will function excessively, so that it is not suitable either. Namely, the above-specified adhering amount will satisfy all requirements for providing preferable effects of the skin-improve as well as preferable feel and softness and, besides, the skin-improving effects with an appropriate durability.

The binders are preferred to be applied onto final products, such as apparel, stockings or the like, which are not further subjected to post-processing. A treating liquid containing a binder such as silicone resins or the like may be coated and dewatered or dried by such a means as not impairing the feel.

As a propellant to be employed in the treating liquid spray of the present invention, liquidized propane or butane, LP gas or the like and mixtures thereof are preferred. The mixing ratio of the propellant to the above-described emulsion is generally 3:97~20:80 (by weight), preferably 5:95~40:60. For a good spraying condition or ironing, known additives such as surfactants, ironing lubricants, glycols, alcohols or the like can be admixed (ironing or hot air drying is conducted preferably at not higher than 130° C.).

Padding materials to be used for the pillows which are particularly important among the bedclothes according to the present invention are not specifically limited in plastics, fibers, wood chips, buckwheat chaff and the like, and preferred, however, to be polyethylene hollow tubes for their air permeability.

As a method for applying the microcapsules containing an aromatic agent with a resinous binder to the paddings for the pillows, mention may be made of a soaking method, spraying method, coating method, or the like. When the hollow tubes are used, the spraying method is preferred. In the soaking method, microcapsules adhering in the hollow portions of the tubes do not contribute to emission of fragrance, since they are not broken, thereby resulting in a low yield. The resinous binders are applied generally in an amount of 0.2-5 times, preferably 0.5-2 times (by weight) that of the microcapsules, to present a sufficient bonding effect.

The pillows according to the present invention emit fragrance as the microcapsules break little by little due to mutual frictions of the padding materials in the pillow, caused by every movement of the head. The feature lies in sound sleep induced at sleepless time, as the more frequently the head moves, the more microcapsules break. On the other hand, since the microcapsules do not break during storing, the fragrance never emits and vanishes.

Best Mode for Carrying out the Invention

Next, explanation will be made by way of an example of the manufacturing process of the above-mentioned skin-improving stockings.

In this manufacturing process, the treatment for applying the microcapsules containing a skin-improver is preferred to be conducted at the time of softening treatment after dyeing and fixing of the stockings, as an excellent treating effect is exhibited efficiently.

On the outset, microcapsules and a binder at a ratio (by weight) of 10:1 ~ 1:5 are fed into a treating machine to prepare a treating bath also containing a softening agent. At this time, each chemical should be fed after having been sufficiently dissolved and diluated in water. Then, when these have been sufficiently homogenized, a buffer agent is introduced. This buffer agent is for controlling hydrogen ion concentration to set and maintain an optimum pH value. As the buffer agent, mention may be made of various materials, such as those comprising, as a main ingredient, a condensed phosphate, which display an excellent pH buffer ability, or the like. However, it is not specifically limited, insofar as it can set and maintain the pH value of the treating bath within the range of 4~6 by its property and amount of feeding. Namely, owing to the fact that making the treating bath acidic will stabilize the treatment with a binder that is weak for alkalis, promote the reaction, and so forth, the bonding force is strengthened between the microcapsules and binder as well as between the microcapsules/binder and knitted fabrics, whereby adsorbability is extremely improved. Accordingly, the pH value of the treating bath is made to be less than 6. However, if the pH value is as too low, as less than 4, the microcapsules and binder coagulate to form a complex which will cause an uneven adhesion, so that it is not suitable. Accordingly, the pH value of the treating bath should be set within the range of 4~6, preferably at a target value of 4.5~5.5.

Then, an appropriate amount of stockings is introduced into this treating bath and heat-treated at 20~80° C. If the treating temperature is lower than 20° C., a satisfactory treating effect can not be obtained, even if the treating time is extended, while if the temperature is higher than 80° C., it is neither good for each chemical nor the stocking and causes problems in quality, so that it is preferred to be within the abovementioned range, particularly 40~60° C. is a usual temperature for softening treatment. Further, as for the treating time, though it relates to temperature, a long time does not necessarily provide an excellent treating effect so that about 15~30 minutes are enough.

Now, the thus obtained, treated stockings are forwarded to a subsequent process comprising dewatering, drying and finish-setting steps and finished articles are produced.

Preferable embodiments of the present invention will be arranged and described hereinbelow.

(a) A microcapsule wherein the ascorbic acid is ascorbyl dipalmitate.
(b) A microcapsule wherein the seaweed extract is an extract liquid of the genus Laminaria belonging to the class Phaeophycease, admixed with JSCI 1,3-butylene glycol.
(c) A microcapsule wherein the antipruritic agent is selected from the group consisting of clemizole phosphate, isothipendyl hydrochloride, diphenhydramine and its derivatives, hydrocortisone and prednisolone.
(d) A microcapsule wherein the analgesic agent is methyl salicylate.
(c) A microcapsule wherein the formaline based resin is a urea-formaline based resin or a melamine-formaline based resin.
(f) A microcapsule wherein the particle diameter is within the range of 5~30 μm.
(g) A microcapsule wherein the wall membrane occupies 5~25% by weight of the microcapsule.
(h) A textile structure wherein the binder forms a rubbery film.
(i) A textile structure wherein the binder is a silicone based resin.
(j) A textile structure wherein the substance having a function to improve physiological conditions of human skin includes at least λ-menthol to also provide refreshing and cool feeling.

The present invention will be explained more concretely hereinafter by way of example.

In the examples, the test for resistance to washing was conducted according to JIS L 0217, 103 Method, and represented by the frequency until the number of adhering microcapsules decreased to 30% or less of the initial number. The percent and part are by weight unless otherwise specified.

EXAMPLE 1

On the outset, microcapsules were manufactured as mentioned below.

Three grams of ascorbyl dipalmitate, 8 g of triglyceride, 9 g of squalane, 6 g of a sodium sulfonated polystyrene and 4 g of urea were added to 300 g of water, the pH was controlled at 4.0 and the temperature was elevated to 40° C. under agitation, to emulsify. Then, 10 g of a 30% formaline aqueous solution was added and the liquid temperature was increased from 40° C. to 70° C. over 15 minutes while agitating at 500 rpm with a laboratory stirrer. Maintaining the temperature at 70° C. for 60 minutes, a polycondensation reaction was carried out. The produced fine particles were separated from the mother liquid by a glass filter and washed with water. Then, after drying in air, heat treatment at 105° C. was conducted for one minute. The obtained microcapsules had a particle diameter of 7~15 μm (averaging 10 μm) and a wall membrane content of 18% by weight.

Then, the under-listed 2 kinds of stockings were knit and dyed and, after a fixing treatment, processed with the above-described microcapsules according to the aforementioned manufacturing process.

Test article: ① Panty stockings.
    Leg portion: 15d/3f Kennel yarn.
    Panty and tow portions:
    30d/8f woolly yarn.
② Panty stockings (support type).
    Leg portion:
    (20 × 13 × 13 DCY) × 13d/3f raw silk yarn.
    Panty portion:
    (20 × 30 POY) × 30d/8f woolly yarn.
    Tow portion:
    13d/3f raw silk yarn × 30d/8f woolly yarn × 70d/18f woolly yarn.

| Binder: | San Softener TAFF A (manufactured by Sanyo Chemical Industries Ltd.) . . . 2% owf. |
|---|---|
| Buffer agent: | Ultra MT (manufactured by Mitejima Kagaku Kogyo Ltd.) |

After processing, drying and finish-setting were performed to provide articles and tests for resistance to washing and feel were conducted.

EXAMPLE 2

As a binder, a forced emulsified type polyurethane aqueous dispersion (Superflex E: manufactured by Daiichi Kogyo Seiyaku K.K.) was used. With regard to microcapsules, test articles and manufacturing processes, those exactly the same as Example 1 were employed.

Articles produced were tested in the same manner as Example 1.

The test results in the above 2 Examples are shown in Table 1.

TABLE 1

| Test Article | | Microcapsules/binder add-on amount (%) | Resistance to washing | feel |
|---|---|---|---|---|
| Example 1 | ① | 1.5/1.5 | 5 | ○ |
|  | ① | 1.0/5.0 | 7 | ○ |
|  | ② | 0.8/4.0 | 8 | △ |
|  | ② | 2.0/1.0 | 4 | ○ |
| Example 2 | ① | 1.5/1.5 | 4 | ○ |
|  | ① | 0.8/4.0 | 5 | ○ |
|  | ② | 1.0/5.0 | 6 | △ |
|  | ② | 2.0/1.0 | 4 | ○ |
| Comparative Example | ① | 1.0/0 | 1 | ○ |
|  | ① | 1.5/0 | 1 | ○ |

As shown in the above Table, the stockings with microcapsules adhering thereto according to the present invention have a sufficient resistance of bonding force to washing and a good feel.

EXAMPLE 3

On the outset, a seaweed extract was manufactured according to the under-described manufacturing process and further microcapsules encapsulating it were manufactured.

Twenty grams of a dry powder of the genus Laminaria belonging to the class Phaeophyceae were admixed with 120 g of JSCI purified water and then extracted at 70~80° C. for 2 hours, followed by filtration to obtain 80 g of filtrate. To this filtrate, 20 g of JSCI 1,3-butylene glycol and 0.3 g of JSCI methyl paraoxybenzoate were added and heated while stirring at 70~80° C. for 1 hour, followed by filtration, to obtain 100 g of seaweed extract.

Then, 3 g of the seaweed extract, 8 g of triglyceride, 9 g of squalane, 6 g of sodium sulfonated polystyrene and 4 g of urea were added to 300 g of water, the pH was controlled at 4.0 and the temperature was elevated to 40° C. under agitation, to emulsify. Then, 10 g of a 30% formaline aqueous solution was added and the liquid temperature was increased from 40° C. to 70° C. over 15 minutes while agitating at 500 rpm with a laboratory stirrer. Maintaining the temperature at 70° C. for 60 minutes, a polycondensation reaction was carried out. The produced fine particles were separated from the mother liquid by a glass filter and washed with water. Then, after drying in air, heat treatment at 105° C. was conducted for one minute.

The obtained microcapsules had a particle diameter of 7~15 μm (averaging 10 μm) and a wall membrane content of 18% by weight.

Then, 2 kinds of stockings, the same as those in the foregoing Example 1, were knit and dyed and, after a fixing treatment, processed with the above-described microcapsules according to the aforementioned manufacturing process.

After processing, drying and finish-setting were performed to provide articles and tests for resistance to washing and feel were conducted.

EXAMPLE 4

As a binder, a forced emulsified type polyurethane aqueous dispersion (Superflex E: manufactured by Daiichi Kogyo Seiyaku K.K.) was used. With regard to microcapsules, test articles and manufacturing processes, those exactly the same as Example 3 were employed.

Articles produced were tested in the same manner as Example 3.

The test results in the above Examples 3 and 4 are shown in Table 2.

TABLE 2

| | Test Article | Microcapsules/binder add-on amount (%) | Resistance to washing | feel |
|---|---|---|---|---|
| Example 3 | ① | 1.5/1.5 | 5 | ○ |
| | ① | 1.0/5.0 | 7 | ○ |
| | ② | 0.8/4.0 | 8 | △ |
| | ② | 2.0/1.0 | 4 | ○ |
| Example 4 | ① | 1.5/1.5 | 4 | ○ |
| | ① | 0.8/4.0 | 5 | ○ |
| | ② | 1.0/5.0 | 6 | △ |
| | ② | 2.0/1.0 | 4 | ○ |
| Comparative Example | ① | 1.0/0 | 1 | ○ |
| | ② | 1.5/0 | 1 | ○ |

As shown in the above Table, the stockings with microcapsules adhering thereto according to the present invention have a sufficient resistance of bonding force to washing and a good feel.

EXAMPLES 5 AND 6

Two grams of clemizole sulfate, 1 g of dλ-camphor, 8 g of lauryl stearate, 9 g of peppermint oil, 6 g of a sodium sulfonated polystyrene and 4 g of urea were added to 300 g of water the pH was controlled at 4.0 and the temperature was elevated to 40° C. under agitation, to emulsify. Then, 10 g of a 30% formaline aqueous solution was added and the liquid temperature was increased from 40° C. to 70° C. over 15 minutes while agitating at 500 rpm with a laboratory stirrer. Maintaining the temperature at 70° C. for 60 minutes, a polycondensation reaction was carried out. The produced fine particles were separated from the mother liquid by a glass filter and washed with water. Then, after drying in air, heat treatment at 105° C. was conducted for one minute.

The obtained microcapsules had particle diameter of 20~30 μm (averaging 24 μm) and a wall membrane content of 18% by weight (Example 5).

Microcapsules containing antipruritics were manufactured in the same manner as Example 5, except that 1.5 g of clemizole sulfate and 1.5 g of diphenhydramine were used (Example 6).

EXAMPLE 7

Thirty grams of the microcapsules containing antipruritics in Example 5 were admixed with 30 g/λ of a silicone based aqueous emulsion comprising, as a main component, an epoxy-modified dimethyl polysiloxane resin. Then, the under-listed 4 kinds of woven or knitted fabrics or cloths were applied on the reverse side thereof (as for the stockings, only on the leg portion) with the above-mentioned emulsion so that the microcapsules might adhere in an amount of 1.5% by weight based on the weight of the fabric or the applied portion of the cloths, then dried and subjected to a heat treatment while wet at 120~130° C. for one minute. The woven or knitted fabrics to which the microcapsules were thus made to adhere were dried according to a conventional method and forwarded to a finish-setting process to provide antipruritic woven or knitted fabrics.

① Plain weave fabric woven with No. 40 count cotton single yarn (gauze)

② Plain weave fabric woven with No. 30 count cotton single yarn (Yukata cloth).

③ Single jersey knitted with No. 40/2 count cotton plied yarn (shirting cloth).

④ Socks plain woven with a No. 60/2 count cotton surface yarn and a 30 denier 2 plied nylon back yarn.

Then, a bandage, Yukata and sport shirt were made up from the above woven or knitted fabrics ①, ② and ③, respectively, and tested for resistance to washing and feel.

TABLE 3

| Test Article | Microcapsules/ binder add-on amount (%) | Resistance to washing | Feel | Remarks |
|---|---|---|---|---|
| ① Bandage | 1.5/1.5 | 5 | ○ | Invention |
| ② Yukata | 1.5/1.5 | 9 | ○ | " |
| ③ Sport shirt | 1.5/1.5 | 12 | ○ | " |
| ④ Socks | 1.5/1.5 | 11 | ○ | " |
| ④' Socks | 0.8/4.0 | 20 or more | △ | " |
| ④" Socks | 1.5/0 | 1 | ○ | Comparative Example |

EXAMPLE 8

On a polyethylene film of 14 cm ×18 cm (many air holes of a 0.5 mm diameter were bored) applied with an adhesive agent, was superimposed an antipruritic bandage of 14 cm ×18 cm, applied with the antipruritic microcapsules of Example 6 in the same manner as that preparing the antipruritic bandage in Example 7. Then, a release paper of 14 cm ×18 cm was laminated to manufacture an antipruritic adhesive sheet.

The antipruritic effect was evaluated by ten panelists. Then, it was found that no unpleasant feeling was felt as that would be felt when an ointment was applied and it displayed an antipruritic effect by being rubbed when one had an itch.

EXAMPLES 9 and 10

Two grams of methyl salicylate, 1 g of λ-menthol, 8 g of lauryl stearate, 9 g of peppermint oil, 6 g of a sodium sulfonated polystyrene and 4 g of urea were added to 300 g of water, the pH was controlled at 4.0 and the temperature was elevated to 40° C. under agitation, to emulsify. Then, 10 g of a 30% formaline aqueous solution was added and the liquid temperature was increased from 40° C. to 70° C. over 15 minutes while agitating at 500 rpm with a laboratory stirrer. Maintaining the temperature at 70° C. for 60 minutes, a polycondensation reaction was carried out. The produced fine particles were separated from the mother liquid by a glass filter and washed with water. Then, after drying in air, heat treatment at 105° C. was conducted for one minute.

The obtained microcapsules had a particle diameter of 20~30 μm (averaging 24 μm) and a wall membrane content of 18% by weight (Example 9).

Microcapsules containing analgesics were manufactured in the same manner as Example 9, except that 2 g of methyl salicylate, 1 g of tocopherol acetate and 1 g of λ-menthol were used (Example 10).

EXAMPLE 11

Thirty grams of the microcapsules containing analgesics in Example 9 were admixed with 30 g/λ of a silicon based aqueous emulsion comprising, as a main component, an epoxy-modified dimethyl polysiloxane resin, to prepare an analgesic treating solution. Then, the underlisted 4 kinds of woven or knitted fabrics or cloths were applied on the reverse side thereof with the above-mentioned analgesic treating solution so that the microcapsules might adhere in an amount of 1.5% by weight based on the weight of the fabric or the applied portion of the cloths, then dried and subjected to a heat treatment while wet at 120~230° C. for one minute. The woven or knitted fabrics to which the microcapsules containing analgesics were thus made to adhere were dried according to a conventional method and forwarded to a finishsetting process to provide analgesic woven or knitted fabrics.

① Plain weave fabric woven with No. 40 count cotton single yarn (gauze)
② Plain weave fabric woven with No. 30 count cotton single yarn (Yukata cloth).
③ Single jersey knitted with No. 40/2 count cotton plied yarn (shirting cloth).
④ Socks plain woven with a No. 60/2 count cotton surface yarn and a 30 denier 2 plied nylon back yarn.

Then, a bandage, Yukata and sport wear were made up from the above woven or knitted fabrics ①, ② and ③, respectively, and tested for the resistance to washing and the feel

TABLE 4

| Test Article | Microcapsules/ binder add-on amount (%) | Resistance to washing | Feel | Remarks |
| --- | --- | --- | --- | --- |
| ① Bandage | 1.5/1.5 | 6 | ◯ | Invention |
| ② Yukata | 1.5/1.5 | 6 | ◯ | Invention |
| ③ Sport shirt | 1.5/1.5 | 12 | ◯ | " |
| ④ Socks | 1.5/1.5 | 10 | ◯ | " |
| ④' Socks | 1.5/—/3 | 4 | ◯ | " |
| ④" Socks | 0.8/4.0 | 20 or more | △ | " |
| ④''' Socks | 1.5/0 | 1 | ◯ | Comparative Example |

EXAMPLE 12

On polyethylene film of 14 cm ×18 cm (many air holes of a 0.5 mm diameter were bored) applied with an adhesive, was superimposed an analgesic bandage of 14 cm ×16 cm, applied with the analgesic microcapsules of Example 10 in the same manner as that preparing the analgesic bandage in Example 11. Then, a release paper of 14 cm ×18 cm was laminated to manufacture an analgesic adhesive sheet.

The analgesic effect was evaluated by ten panelists. Then, it was found that no unpleasant feeling was felt as that would be felt when an ointment was applied and it displayed an analgesic effect by being rubbed when one had an ache.

EXAMPLE 13

A polyester based polyurethane spun-bond nonwoven fabric (unit weight: 80 g/m$^2$, and diameter of single filament: 20~30 μm) was soaked in a mixed liquid (analgesic processing liquid) comprising 30 g/λ of the analgesic microcapsules of Example 10 and 30 g/λ of the silicone based aqueous emulsion of Example 11, each of which adhered in an amount of 1.5% by weight.

Then, a piece of the fabric 12 cm wide and 25 cm long was cut out, both ends of which were joined to each other with a hot roll to fabricate an integral, analgesic supporter of a 24 cm circumference.

The analgesic effect was evaluated by 10 panelists who were tennis players and it was found that the supporter was excellent in fittability and airpermeability when it was worn, and displayed an analgesic effect by being rubbed when one felt fatigue or muscle ache.

EXAMPLES 14 AND 15

On the supporter made of the polyurethane nonwoven fabric of Example 13, the analgesic processing liquid of Example 13 was sprayed and fixed by ironing. The add-on amount of the analgesic microcapsules was about 1.0% by weight based on the weight of the supporter (Example 14).

An analgesic processing liquid prepared by changing the amounts of both the analgesic microcapsules and silicone based resin in Example 13 to 60 g/λ, was put into an aerosol can and liquidized propane gas (internal pressure at 20° C. of 3.1 kg/cm$^2$) was charged at a weight ratio of the analgesic processing liquid/the gas=70/30. Then, in the same manner as Example 14, the supporter of the polyurethane nonwoven fabric was sprayed with the liquid and ironed (Example 15).

Both the analgesic effect and wearability were as good as Example 13. Further, as the result of the test for resistance to washing, it was found that all displayed an analgesic effect by being rubbed until washing was repeated 4~6 times.

EXAMPLE 16

Microcapsules containing analgesics were manufactured in the same manner as Example 9, except that 1 g of methyl salicylate and 2 g of λ-menthol were used as analgesics and lauryl stearate was replaced by an acrylic acid copolymer.

Then, 2 kinds of stockings, the same as the foregoing Example 1, were knitted and dyed and, after finishing a fixing treatment, a processing treatment to apply the above-mentioned analgesic microcapsules was carried out in the same manner as Example 1.

After the processing treatment, drying and finish-setting were conducted to produce articles which were then tested for resistance to washing and feel.

EXAMPLE 17

As a binder, a forced emulsified type polyurethane aqueous dispersion (Superflex E: manufactured by Daiichi Kogyo Seiyaku Co., Ltd.) was used. Exactly the same microcapsules, test articles and manufacturing process as Example 16 were employed.

The articles thus produced were tested in the same manner as Example 16.

The test results in the above Examples 16 and 17 were shown in Table 5.

TABLE 5

| | Test Article | Microcapsules/binder add-on amount (%) | Resistance to washing | feel |
|---|---|---|---|---|
| Example 16 | ① | 1.5/1.5 | 5 | ○ |
| | ① | 1.0/5.0 | 7 | △ |
| | ② | 0.6/3.0 | 7 | ○ |
| | ② | 2.0/1.0 | 4 | ○ |
| Example 17 | ① | 1.5/1.5 | 4 | ○ |
| | ① | 0.6/3.0 | 5 | ○ |
| | ② | 1.0/5.0 | 6 | △ |
| | ② | 2.0/1.0 | 4 | ○ |
| Comparative Example | ① | 1.0/0 | 1 | ○ |
| | ② | 1.5/0 | 1 | ○ |

As shown in Table 5, the stockings having the microcapsules of the present invention adhering thereto exhibit a sufficient resistance of adhering force to washing as well as a good feel, and further display cool and refreshing feeling and analgesic effect by being rubbed.

EXAMPLE 18

Fragrance processing liquids were obtained by mixing 50 parts each of aqueous dispersions of 40% microcapsules composed of a micro-envelope formed by polycondensation of methylol melamine, containing an aromatic oil of jasmine, sandalwood, rose or eucalyptus in an amount of 30%, 50% and 80%, respectively, (see Table 1, particle diameter: 5~10 μm) with 50 parts of an aqueous emulsion of 50% vinyl acetate. Five parts of the fragrance processing liquid were sprayed onto 95 parts of polyethylene hollow tubes for paddings, having a wall thickness of 0.3 mm, an outside diameter of 5 mm and a length of 7 mm and, after mixing lightly, the tubes were dried at 60° C. for 4 hours in a hot flue. In the course of drying, 2 hours after the commencement of drying, tubes were lightly mixed to prevent sticking to each others. Twenty percent of the thus obtained hollow tubes having the microcapsules containing an aromatic agent adhering thereto were mixed in usual hollow tubes and stuffed in an inner net sack of a pillow case to manufacture a fragrant pillow. By 12 each of male and female panelists 30~35 years old, the above 12 pillows were tested for sound sleeping. The bed room was made to be in unpleasant conditions at a temperature at about 25° C. and a relative humidity of 70%. The next morning, the following results were obtained by questionnaire:

(1) All panelists answered that the pillows containing an aromatic agent induced sound sleeping more than the usual pillows.

(2) As for the kinds of aromatic agents, sandalwood, jasmine, rose and eucalyptus were preferred in this order.

(3) As for the content of the aromatic agents, 80% was generally preferred, except that as for eucalyptus, 30% is preferred to 80%, since some panelists were of the opinion that its fragrance was too strong.

The washing test was conducted by washing the hollow tubes with a neutral detergent solution for 2 hours, followed by washing with water for 10 minutes. Then, the effect of fragrance emission did not substantially change after washing. Further 10 cycles of washing operation did not substantially change the effect.

TABLE 6

| Test No. | Kind of Aromatic Oil | Content of Aromatic Oil (wt. %) |
|---|---|---|
| 1 | Jasmine | 30 |
| 2 | Jasmine | 50 |
| 3 | Jasmine | 80 |
| 4 | Sandalwood | 30 |
| 5 | Sandalwood | 50 |
| 6 | Sandalwood | 80 |
| 7 | Rose | 30 |
| 8 | Rose | 50 |
| 9 | Rose | 80 |
| 10 | Eucalyptus | 30 |
| 11 | Eucalyptus | 50 |
| 12 | Eucalyptus | 80 |

EXAMPLE 19

Forty grams per liter of microcapsules of a urea based resin containing an aromatic agent (jasmine-like fragrance, average particle diameter: 8 μm, and wall membrane thickness: 1 μm) were mixed in 80 g/λ of a silicone based aqueous emulsion comprising an epoxymodified dimethyl polysiloxane resin as a main ingredient. This mixed emulsion was put into an aerosol can and liquidized propane gas (internal pressure at 20° C. of 3.1 kg) was charged at a weight ratio of the mixed emulsion/the gas=70/30. Then, the emulsion was sprayed onto the under-mentioned panty stockings and fixed by ironing (the add-on amount of the fragrant microcapsules was made to be about 0.5% by weight based on the weight of the fabric in the adhering portion). As the result of the test for resistance to washing, according to JIS L 0217, 103 Method, it was found that the stockings emitted fragrance by being rubbed until washing was repeated 3~6 times.

| Panty stockings (support type). | |
|---|---|
| Leg portion: | (20d/1f polyurethane × 13d/3f × 13d/3f DCY) × 13d/3f raw silk yarn. |
| Panty portion: | (20d/1f polyurethane × 30d/8f POY) × 30d/8f woolly yarn. |
| Tow portion: | 13d/3f raw silk yarn × 30d/8f woolly yarn × 70d/18f woolly yarn. |

EXAMPLE 20

A mixed emulsion which was prepared by changing the content of the silicone based aqueous emulsion to 40 g/λ in Example 19, was sprayed upon a one-piece dress (made of georgette; polyester/rayon=50/50) and then fixed by ironing.

As the result of the test for resistance to washing, according to JIS L 0217, 401 Method, it was found that the dress emitted fragrance by being rubbed until washing was repeated 4~7 times.

EXAMPLE 21

A fragrance processing agent for spray which was prepared by changing the silicone based resin in Example 19 to a hydroxypropylated starch, was sprayed upon sheeting (plain weave of 120×76/inch, with No. 45 count yarn of polyester/cotton=35/65) and fixed by ironing.

EXAMPLE 22

A panty stocking was soaked in a mixed emulsion prepared by changing the contents of the microcapsules and silicone based aqueous emulsion in Example 19 to 10 g/λ and 20 g/λ, respectively, and fixed by ironing.

The thus obtained fragrant panty stocking emitted an adequate fragrance caused by gradual breakage of microcapsules while it was worn or subjected to intentional application of friction thereto. This effect remained effective until the stocking was washed 3~6 times.

Industrial Applicability

When one wears the stockings according to the present invention, the microcapsules are broken little by little by friction while wearing, and encapsulated ascorbic acids, tocopherols or seaweed extracts are exposed and naturally contact with one's legs to provide a whitening or moisturizing effect thereto and also preserve the humidity of the skin.

Accordingly, when going out, one can wear these stockings in such a sense as if one wore a usual whitening lotion, humidity preservable lotion or the like on one's legs before going to bed, so that the stockings can respond consumers' needs as a high value added article.

Alternatively, the textile structures of the present invention having microcapsules containing antipruritics or analgesics adhering thereto, display an antipruritic effect or analgesic effect (including cool and refreshing feeling), since the microcapsules are broken little by little when the structures are used or subjected to intentional application of friction thereto. Accordingly, the effect does not vanish instantly owing to sustained emission and has sufficient lastingness.

Further, by providing a binder to the microcapsules at an appropriate ratio, bonding force and adhesivity are noticeably improved, whereby aimed add-on amount and durability of antipruritic effect or analgesic effect are acquired.

Further, the processing process requires no complicated processing steps and enables sure manufacture of the fibers or textile structures according to the present invention by applying thereto a treating agent prepared by mixing microcapsules with a binder at an appropriate ratio, followed by heat treatment.

Further, by providing a binder to the microcapsules at an appropriate ratio, bonding force and adhesivity are noticeably improved, whereby aimed add-on amount and resistance of effect to washing are acquired.

The processing liquid and its spray according to the present invention are applied to textile structures or the like by means of spraying or soaking, and fixed by drying with an iron or hot air dryer, so that they are also suitable for home use.

Furthermore, regarding the paddings and pillows, since microcapsules encapsulating an aromatic agent are used, little of fragrance vanishes or is transferred to other materials during storage, so that the effect lasts long.

Since the microcapsules containing an aromatic agent are made to adhere to the paddings of the pillow, washing can be conducted with less washing cycles under milder washing conditions.

The pillows according to the present invention emit fragrance upon every movement of the head and can be used effectively.

The fragrance processing liquid and its spray according to the present invention are applied to textile structures or the like by means of spraying or soaking, and fixed by ironing, so that they are also suitable for home use. Thus, this invention has numerous advantages.

We claim:

1. A textile structure having microcapsules adhered thereto by a binder, said microcapsules having a particle diameter in the range of 2~40 μm and a wall membrane comprising a synthetic high molecular material and encapsulating a substance for improving physiological conditions of the human skin, said substance selected from the group consisting of ascorbic acids, tocopherols, seaweed extracts, antipruritics and analgesics, said microcapsules and binder being in a weight ratio in the range of 10:1~1:5, the total amount of both the microcapsules and binder being 0.3~15% based on the weight of the portions of the fibers to which the microcapsules and binder are adhered to.

2. The textile structure claimed in claim 1, which is a stocking.

3. The textile structure claimed in claim 1, which is an underwear.

4. The textile structure claimed in claim 1, wherein said microcapsules have a wall membrane thickness of from 0.3~4 μm.

5. The textile structure claimed in claim 1, wherein said microcapsules have a wall membrane thickness of from 0.53~2 μm.

6. The textile structure claimed in claim 1, wherein said substance is an ascorbic acid.

7. The textile structure claimed in claim 1, wherein said substance is a tocopherol.

8. The textile structure claimed in claim 1, wherein said substance is a seaweed extract.

9. The textile structure claimed in claim 1, wherein said substance is an antipruritic agent.

10. The textile structure claimed in claim 1, wherein said substance is an analgesic agent.

11. A textile sheet material, wherein a first textile fabric, having microcapsules adhered thereto by a binder, is laminated with a second textile fabric or sheet, said microcapsules having a particle diameter in the range of 2~40 μm and a wall membrane comprising a synthetic high molecular material and encapsulating a substance for improving physiological conditions of the human skin, said substance being selected from the group consisting of ascorbic acids, tocopherols, seaweed extracts, antipruritics and analgesics.

* * * * *